United States Patent [19]

Le Pivert

[11] 4,252,130
[45] Feb. 24, 1981

[54] METHOD AND APPARATUS FOR MONITORING THE CONGELATION OF A BIOLOGICAL BODY

[75] Inventor: Patrick Le Pivert, Saint Etienne, France

[73] Assignee: Agence Nationale de Valorisation de la Recherche, Neuilly sur Seine, France

[21] Appl. No.: 859,520

[22] Filed: Dec. 12, 1977

Related U.S. Application Data

[63] Continuation-in-part of Ser. No. 625,075, Oct. 23, 1975, abandoned.

[30] Foreign Application Priority Data

Oct. 29, 1974 [FR] France .............................. 74 36053
May 23, 1975 [FR] France .............................. 75 16120

[51] Int. Cl.³ ........................................ A61B 5/05
[52] U.S. Cl. ............................. 128/734; 128/303.1; 324/65 R
[58] Field of Search ............. 128/2.1 Z, 2.1 R, 2.1 M, 128/303.1, 734; 324/65 R

[56] References Cited

U.S. PATENT DOCUMENTS

| | | | |
|---|---|---|---|
| 2,734,166 | 2/1956 | Hooker | 128/2.1 Z X |
| 3,070,746 | 12/1962 | Moore et al. | 324/65 R |
| 3,316,896 | 5/1967 | Thomasset | 128/2.1 Z |
| 3,320,946 | 5/1967 | Dethloff et al. | 128/2.1 Z |
| 3,347,223 | 10/1967 | Pacela | 128/2.1 Z |
| 3,563,231 | 2/1971 | Ducote et al. | 128/2.1 M |
| 3,665,302 | 5/1972 | Lees et al. | 324/65 R X |
| 3,802,419 | 4/1974 | Yates | 128/2.1 R |
| 3,905,355 | 9/1975 | Brudny | 128/2.1 M |
| 3,924,609 | 12/1975 | Friedenberg et al. | 128/2.1 R |
| 3,971,366 | 7/1976 | Motoyama | 128/2.1 Z |

FOREIGN PATENT DOCUMENTS 187213 11/1966 U.S.S.R. .............................. 128/2.1 Z

OTHER PUBLICATIONS

Geddes et al., "The Measurement . . . Impedance", Am J. of Med. Elec., Jan.-Mar. 1964, pp. 16-27.

Primary Examiner—Lee S. Cohen
Attorney, Agent, or Firm—Edwin E. Greigg

[57] ABSTRACT

The method and apparatus determines the moment when, in the course of an operation of freezing a biological body of predetermined contour, the freezing becomes complete. At the periphery of the body are implanted at least two electrodes for monitoring the impedance of the body between said electrodes. The electrodes are connected to the terminals of an impedance measuring head and of an alternating current generator. The variations of this impedance are a function of the state of freezing said body. The moment when this impedance becomes very high corresponds to complete freezing of the body between the electrodes.

1 Claim, 2 Drawing Figures

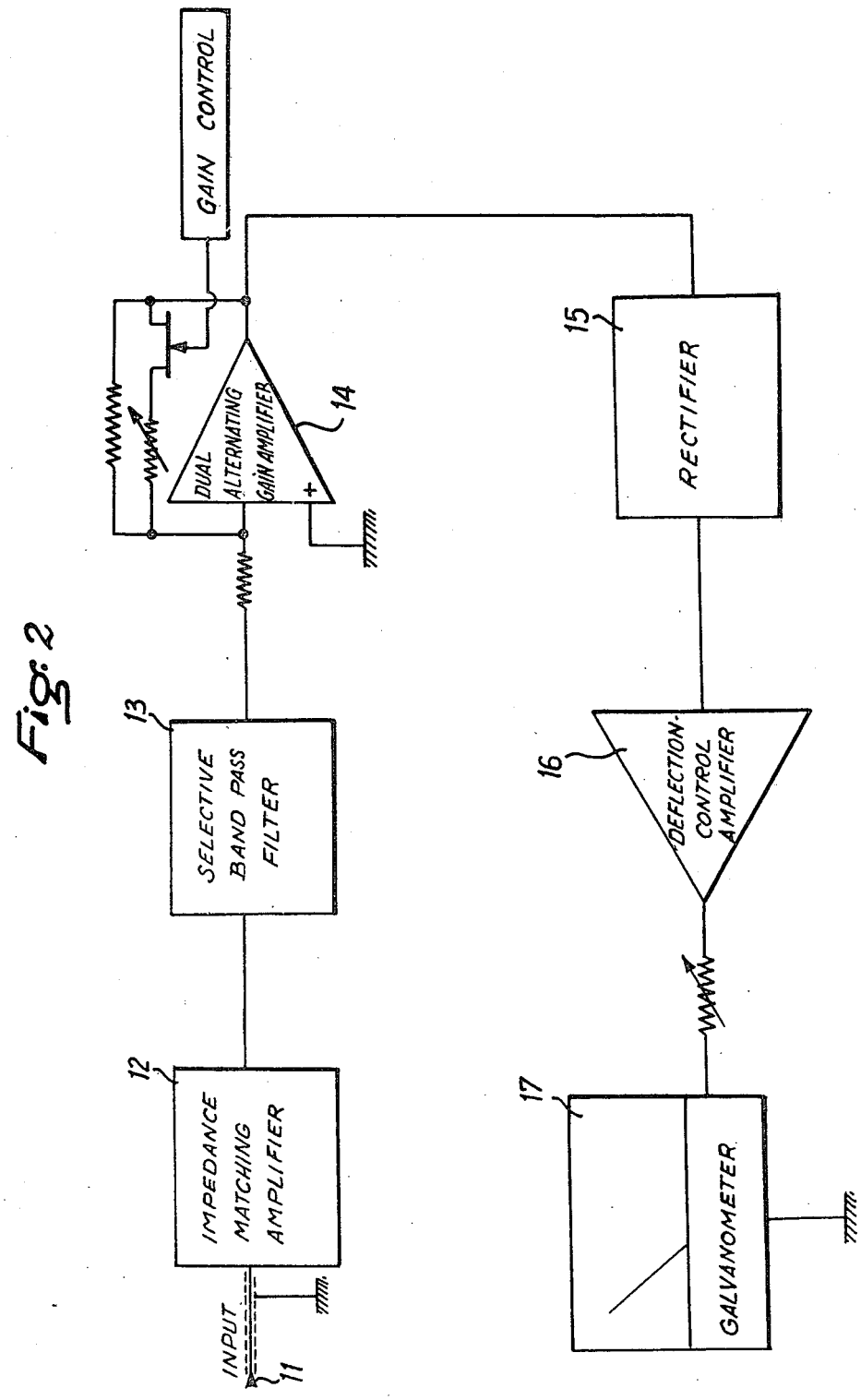

METHOD AND APPARATUS FOR MONITORING THE CONGELATION OF A BIOLOGICAL BODY

RELATED APPLICATIONS

This application is a continuation-in-part of application U.S. Ser. No. 625,075, filed Oct. 23, 1975 now abandoned.

BACKGROUND OF THE INVENTION

The invention relates to a method for determining the moment when, in the course of an operation of freezing a biological body of a predetermined shape, the freezing becomes complete.

The invention also relates to an automatic apparatus for monitoring the impedance of biological bodies, more especially that impedance produced in applying the aforesaid method.

The apparatus according to the invention, which is called hereinafter an "impedometer" is particularly valuable for resolving the difficulty which exists in determining the state of complete congelation of a mass of tissue which it is proposed to remove by the surgical technique based upon cryonecrosis.

An apparatus of this type is designed to be integrated into a complete cryosurgical assembly thus greatly facilitating the clinical use of the latter.

In point of fact, the object of cryosurgery is to destroy all the cells of unhealthy tissue while sparing the neighboring healthy tissue to the maximum extent.

The achievement of this result implies, as a preliminary that after having estimated the substantially exact limits of the unhealthy tissue or organ, the determination of the exact conditions of congelation to insure "cryodestruction" as complete as possible within the "target" space. By "target" space is meant the whole of the unhealthy cellular mass which it has been decided to destroy.

Now, when a certain amount of heat is extracted from a biological system, there is a change of phase or change of state which converts the freezable water into ice and has the result of "extracting" from the cell the water of solvation and the "structural" water, in particular the membranous water. Considering that in an aqueous system, water crystallizes first in the form of pure ice, dehydration occurs. Since the stability of a biological system is dependent on the maintenance of an exact concentration of aqueous solutions, the consequences of the loss of the water of solvation incorporated in the crystalline structure of the newly formed ice will be more or less important for the equilibrium of this system; moreover, the concentrated solution will be located between the ice crystals.

It is easy to foresee that the disappearance of "structural" water, necessary for molecular and intermolecular functions will involve changes which are often irreversible, and incompatible with cellular survival. One can then understand the alterations in the membrane systems.

The destructive potential of cryosurgery thus appears to be directly related to the cellular changes caused by the changes of state of the water.

These considerations are known to be confirmed by experiments on tumors produced in animals such as the rat.

It is also known that immediate or short term cryodestruction is all the more complete if the freezing of the unhealthy tissue is effected at a sufficiently high speed.

Now, for freezing produced by means of a cryode, operating, for example, by the projection of a jet of liquid nitrogen, 60 to 70% of the maximum freezing effect will be achieved in the first 30 seconds of cooling and 80 to 90% in about five minutes.

Hence there is no advantage in prolonging the freezing action of the cryode beyond five minutes; and besides, beyond this limit, the thermal conductivity of the tissues conjugated with the very low temperatures of the cryode (which can be of the order of $-200°$ C.) would risk causing the freezing of an "envelope" of neighboring healthy tissue which would not be tolerable. It may be considered desirable for this envelope to be limited to 5 to 10 mm in thickness, which signifies that, taking into account the foregoing, the action of the cryode should be interrupted with high accuracy to effect the complete congelation of the unhealthy tissue.

It is known in the art, to determine the state of congelation of the mass of unhealthy tissue to be treated, by the use of probes constituted by thermocouples. These probes have the drawback of only giving a valid indication for the place where they are implanted. On the other hand, they are not reliable since a part of the probe can be in contact with tissue actually frozen while its point is in contact with tissue which is not yet frozen. Now, in such as case, it will nonetheless give the indication of congelation.

OBJECTS AND SUMMARY OF THE INVENTION

It is therefore an object of the ivention to provide an improved method for determining the moment and/or extent of complete congelation in freezing techniques.

The inventer has observed that in a biological medium the complete congelation of the water contained in the tissue involves an increase in the electrical resistance of the medium concerned to such an extent that it ceases to be measurable, and that, on the other hand, the resistance remains measurable as long as liquid veins remain in the medium to be frozen.

It is therefore an object of the invention to provide a method for monitoring the variations of tissue resistance in the course of congelation (and also of decongelation) to give an accurate indication as to whether the treated tissue is in a state of complete or incomplete congelation.

Accordingly, according to the invention, there is provided a method comprising implanting in the periphery of the body to be frozen, at least two electrodes connected to means for monitoring the impedance of the body between said electrodes to determine the variations in this impedance which are a function of the state of congelation of said body, and more particularly to determine the moment when this impedance becomes very high and which corresponds to complete congelation.

According to another aspect of the invention there is provided an apparatus having at least two electrodes for implantation in the body to be frozen, connected to the terminals of an impedance measuring head and to an alternating current generator.

The resistance of the tissues and its variation can be measured by means of an ohmmeter operating at constant current and which gives the value of this resistance measured between two electrodes implanted in the tumorous tissue and, preferably, at its periphery and in diametrically opposite position with respect to the approximate center of the tumor. This very simple and positive apparatus has a major drawback; it is necessary to have a considerable current to be able to neglect the interference of a counter electromotive force resulting from the polarization of the electrodes. This results in scorching of the tissues at the anode, and release of gas at the cathode. In practice, these phenomena of polarization, even though minimized, can falsify the results.

To overcome this drawback, according to the invention there is provided tissue resistance measuring means comprising an impedometer supplied by an alternating current source. The frequency selected is for example of the order of 1,000 or some thousands of hertz. Any phenomenon of tetanization is thus avoided and, of course, any interference due to the polarization of the electrodes. However, it is possible advantageously to effect measurements at high frequency.

Measurement of the impedance can be effected by means of a constant current, produced by a suitable generator. However, it has been observed that to watch the state of congelation of the treated body, it was not necessary to have linearity between the difference of potential assured between the electrodes and the resistance of the body existing between these electrodes. In other words, the measurement remains based on the voltamperemetric principle which uses one source of voltage. However, for measurements at normothermy in which the tissue resistance can be relatively low ($\leq 1000\Omega$) a substantially constant current will be produced (for example 10 $\mu A$) by means of a high resistance for example 300 k $\Lambda$ connected to the output of the generator.

When measurements are taken during freezing of a biological body, the freezing is stopped when substantially the difference of maximum potential of the generator, which is 3 volts in the example above, appears across the electrodes, corresponding to a very rapid increase in the intra-cellular resistance of the biological body to about 10 mega-ohms, which is much higher than the generator output impedance.

The invention provides a measuring head particularly well adapted to this type of measurement, both in normothermy and in the course of congelation.

In fact it is advantageous to provide the apparatus with more than two pairs of electrodes and preferably eight pairs. Thus, a plurality of pairs of electrodes enables the tissue congelation to be monitored in a complex space and in various successive zones, since it is difficult and in practice of little advantage to move the electrodes in the course of freezing. Furthermore, this enables, for example, the observation and the measurement in almost simultaneous manner, of the freezing of one zone and the thawing of another zone. Lastly, this arrangement enables the homogeneity of freezing to be watched in a specific zone.

According to another feature of the present invention, there is provided an apparatus which includes a plurality of pairs of electrodes, for implantation in the periphery of a body, characterized in that all the pairs of electrodes are connected to a switching control for bringing into circuit successively, and at will, each of them with an alternating current generator and a measuring head capable of measuring the impedance of the body between a pair of electrodes selected by the switching control.

The switching control is preferably constituted by a rotary switch and/or pulse push-button contact controlling a logic system which converts the signal and effects the selected connection. The pairs of electrodes can be plugged in by means of connecting wires to control means connected electrically to a box which contains the generator and the measuring head. The control means may be a sterilizable desk placed within the reach of the surgeon, enabling the latter to manipulate the appropriate control responsive to the indications of the measuring head.

The tissue resistance monitoring means according to the invention is advantageously integrated e.g. by servocoupling means, into a complete cryosurgical apparatus providing notably measurements of the liquid nitrogen level of an autopressurized container with setting of the level and "insufficient level" warning and effecting the functions of control and pressurization of the container and withdrawal of the liquid nitrogen.

BRIEF DESCRIPTION OF THE DRAWINGS

The invention will be better understood and other advantages and features will appear upon reading the following description of one embodiment of the invention with reference to the accompanying drawings, given purely by way of non-limiting example. In the drawings;

FIG. 2 is a block diagram of a preferred embodiment of a measuring head according to the invention.

DESCRIPTION OF THE PREFERRED EMBODIMENT

Figure 1:
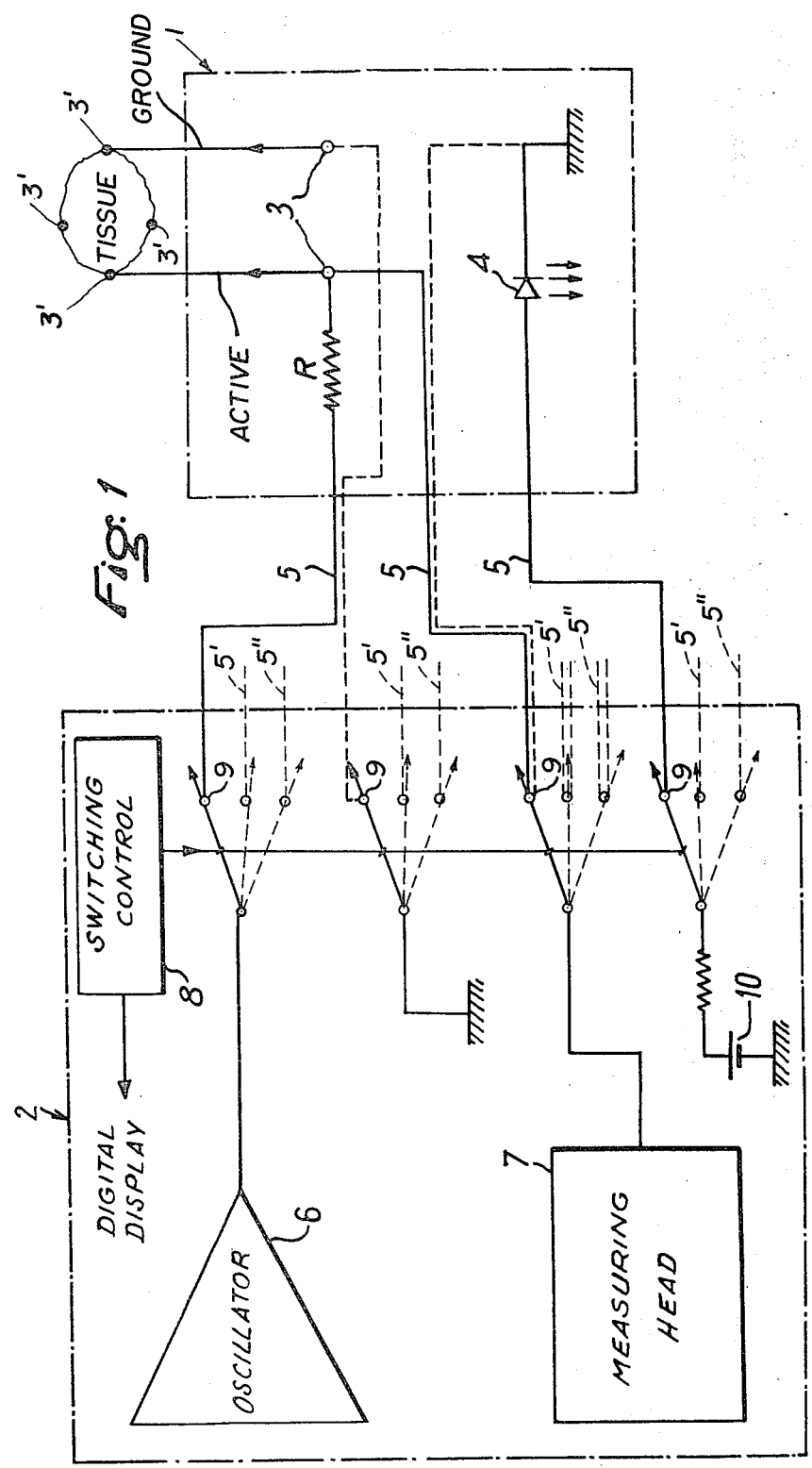
FIG. 1 is a diagrammatic view of the whole of the device.

The device is advantageously arranged in two distinct assemblies, a control desk 1 and a box 2. In order to make the diagrams clearer only the connections relating to one pair of electrodes are shown. In the same way, the switching for three pairs of electrodes only is drawn although a preferred embodiment includes in fact eight pairs of electrodes.

A control desk 1 comprises eight connector sockets (one only is shown at 3) for eight pairs of electrodes (only one pair shown at 3'). Advantageously these sockets are actually jacks, each designed to receive a single coaxial plug connected to a pair of electrodes 3', the coaxial cable being separated at ten centimeters, for example, from said pair. A resistor R, of 300 K $\Omega$ for example, is connected to the active part of the socket. In addition, to each socket is attached a light emitting diode 4 intended to serve as a single lamp as will be explained below.

The control desk 1 is connected electrically to the box 2 by shielded connecting cables such as 5 of low impedance. The box 2 includes an oscillator 6, for example of 1 K Hz and voltage and output impedance of 3 volts and 50 $\Omega$ respectively. It may however be advantageous to provide a high frequency generator adjustable to a frequency as a function of the electrical and biological criteria of the specimen.

The box 2 includes also an impedance measuring head 7 and a switching control 8. This control in the form, for example, of a rotary switch, is intended to switch the oscillator and the measuring head to a particular pair of electrodes. For this purpose a series of four studs such as 9 per pair of electrodes enables the simultaneous connection respectively of the oscillator and of said pair (two studs of which one is to ground), and of the measuring head and, lastly, one stud for the application of voltage to the corresponding light emitting diode 4 by means, for example, of a battery 10. Three of the various positions for the switching control 8 are shown in FIG. 1, the first position being shown in solid lines for connection to the cables 5 and the other two positions shown in broken lines for connection to cables 5' and 5", respectively, also shown in broken lines.

The switching control is advantageously provided with a digital display (seven segment display device for example) so as to show the pair of electrodes in operation. Another switching control (not shown) may be provided on the control desk to enable the surgeon to switch in the desired pair of electrodes. This control is preferably a pulse push button acting on a decade logic system which counts the pulses. To enable the successive use of the pulse button and of the rotary switch, the latter includes as many positions plus one as the number of pairs of electrodes, one distinct position being allocated to each of said pairs while the additional position brings the logic system into circuit.

FIG. 2 shows diagrammatically a measuring head according to the invention.

This measuring head includes an input 11 followed by the following series of electronic components; an impedance matching amplifier 12, a selective band-pass filter 13, an alternating dual gain amplifier 14, a rectifier 15, a deflection control amplifier 16 and a dual scale galvanometer 17 of the ohmmeter type. The impedance matching amplifier is preferably provided with field effect transistors and an input impedance greater than $10^9$ Ω, the selective filter has an overvoltage of 20 db at 1000 Hz and the rectifier has a low stray voltage obtained for example by means of operational circuits. In addition, the alternating amplifier is advantageously an operation amplifier whose gains are controlled by voltage by means of a field effect transistor. The galvanometer is preferably ferromagnetic and the deflection control amplifier of the voltage follower "booster" type.

This arrangement is particularly reliable and enables an automatic change of range. In fact, when it is desired to effect a measurement of low impedance (0 to 2000 Ω) in normothermy or on the other hand, at high impedances at the moment of congelation, it is possible, due to the dual gain amplifier, to select the most suitable and to read the result of the measurement on the corresponding scale of the galvonometer.

Advantageously, a sound signal (not shown) indicating the end of freezing is provided, for example, in the measuring head. This signal is triggered when the resistance measured is judged sufficient.

In order to rapidly localize any faulty element and, if necessary, to replace it rapidly, the electronic assembly is divided into a plurality of printed circuits in the form of cards each intended to constitute a module effecting one particular function, such as:

a symmetrical supply with regulator integrated circuits a Wien bridge generator, followed by an impedance reducer and an end of congelation detector controlling a sound system which uses the frequency of the generator the measuring head logic systems (decade, decoding, display drive . . .)

switching with relays range switch.

The device described as a whole in FIG. 1 is obviously intended to be integrated, as has already been stated, into a complete cryosurgical apparatus. This apparatus effects notably in addition the measurement of the liquid nitrogen level of an auto-pressurized container with level display and "insufficient level" alarm and effects the functions of control of pressurization of the container and of withdrawal of the liquid nitrogen. This measurement and these functions are provided by means of electronic components which are advantageously in the form of printed circuits and servocoupled to form an assembly of modules with those belonging to the impedance monitoring device.

The use of the device is simple to understand. The electrodes 3' are first implanted at the periphery of the tissue to be treated and plugged by their connecting wires into the corresponding sockets provided in the control desk 1. In the course of freezing, of thawing or again in normothermy, the surgeon can effect a series of measurements to analyze the state of the tissue after having adjusted the desired gain. For this, the surgeon or an assistant manipulates the rotary switch, or the pulse push-button, so as to connect the pair of electrodes with which he desires to effect the measurement. This switching displays numerically the number of the pair selected and lights the corresponding control signal lamp, while the result of the measurement is read on the galvanometer. In addition, in the course of freezing, the sound signal, provided if necessary, warns the surgeon of the state of freezing of the tissue judged sufficient.

It is obvious that numerous modifications can be envisaged without departing from the scope of the invention and notably in the choice of components and their arrangement. Moreover, although the device described is principally intended for the automatic measurement of the impedance of tissues "in vivo", cancerous for example, in the course of freezing or of thawing, it is also applicable, for example, to measurements of the freezing kinetics of biological products in vitro, to freeze drying and to the preservation of foodstuffs.

What is claimed is:

1. A method for determining the moment, in the course of an operation, of freezing of a portion of a biological body in which the body portion is defined by a predetermined contour including the steps of:

implanting at least one pair of electrodes in oppositely disposed locations on the periphery of said body portion, subjecting said body portion to a quick freezing operation, measuring the impedance variations of said body portion between said at least one pair of electrodes during said freezing operation, and terminating said freezing operation when said measured impedance variations indicate that said body portion has reached the desired state of freezing whereby the body portion is cryogenically destroyed and damage to the tissue of said body surrounding said body portion is avoided.

* * * * *